United States Patent [19]

Kirschenberg et al.

[11] Patent Number: 4,709,692
[45] Date of Patent: Dec. 1, 1987

[54] THIGH MOUNTED LOWER BACK SUPPORT BELT

[76] Inventors: Bruce H. Kirschenberg, 2811 Pine Island Rd. N., Sunrise, Fla. 33300; Richard L. Platt, 1440 NE. 43rd Ct., Pompano Beach, Fla. 33064

[21] Appl. No.: 881,451

[22] Filed: Jul. 2, 1986

[51] Int. Cl.⁴ ............................................. A61F 5/02
[52] U.S. Cl. ......................................... 128/78; 2/44; 450/94; 450/100; 450/114
[58] Field of Search ..................... 128/78, 518 R, 520, 128/524, 538; 2/44

[56] References Cited

U.S. PATENT DOCUMENTS

| | | | |
|---|---|---|---|
| 1,386,067 | 8/1921 | Mason | 2/45 |
| 1,469,687 | 10/1923 | Pfaltzgraff | 128/530 |
| 1,812,529 | 6/1931 | Haulbrook et al. | 128/78 |
| 2,778,358 | 1/1957 | Keles | 128/78 |
| 2,891,253 | 6/1959 | Blatt | 2/313 |
| 2,904,793 | 9/1959 | Blatt | 2/313 |
| 3,411,500 | 11/1968 | Gatts | 128/68 |
| 3,524,449 | 8/1970 | Peters | 128/524 |
| 4,475,543 | 10/1984 | Brooks et al. | 128/78 |
| 4,497,315 | 2/1985 | Fettweis et al. | 128/78 |
| 4,574,790 | 3/1986 | Wellershaus | 128/78 |

Primary Examiner—Edgar S. Burr
Assistant Examiner—Moshe I. Cohen
Attorney, Agent, or Firm—Oltman and Flynn

[57] ABSTRACT

The thigh mounted lower back support belt works to keep the human spine straight while bending. This added support for the lower back aids persons engaged in aerobics, golf, lifting, and prolonged sitting. Full flexibility of motion is possible while easing the support load of the lower back. Thigh straps attach to a waist belt which pulls the stomach back while bending.

2 Claims, 3 Drawing Figures 4,709,692

THIGH MOUNTED LOWER BACK SUPPORT BELT

FIELD OF THE INVENTION

The present invention relates to a lower back support belt.

BACKGROUND OF THE INVENTION

One of the most common physical ailments is lower back pain. Many causes of lower back pain exist. Most common among them are postural defects. There should be a normal "forward curve" or "lordosis" to the lower back known as the lumbar region. Poor abdominal muscle tone or congenital defects or injuries can cause an increased forward tilt of the pelvis. This is known as lumbar lordosis. The condition causes much greater force on the vertebrae and discs of the lower back. This greater force creates a susceptibility to the vertebrae moving out of place, a condition termed vertebral subluxations, or increased wearing down of the discs termed disc degeneration, or a pinched nerve termed nerve root irritation.

Known lumbo-sacral belts merely provide abdominal support while limiting physical activity. No belt known by applicant allows comparable flexible movement while supporting the lower back.

SUMMARY OF THE INVENTION

An object of the present invention is to support the lower back by urging the spine straight while at the same time allowing natural movement of the upper torso.

Another object of the present invention is to utilize the thighs as a support basis for the supporting belt.

Other objects of this invention will appear from the following description and appended claims, reference being had to the accompanying drawings forming a part of this specification wherein like reference characters designate corresponding parts in the several views.

The present invention provides the most support to the lower back, *not* to the abdomen which is common in garter type belts.

Thigh straps anchor vertical buttocks straps which in turn support the gluteal muscles. The vertical buttocks straps attach to the hip strap. The hip strap goes over the top of the hips known as the iliac crest. The hip strap narrows at the ends which fasten at the navel.

Any time the knees are bent the thigh straps move forward, thus pulling the vertical buttocks straps which in turn pulls the hip strap thereby rotating the pelvis backward. This flattens the forward curvature of the lower spine during the time the knees are flexed.

Thus, in a golfer's stance or various aerobic activities where the back is placed in positions of instability the present invention helps prevent excessive curvature with the resultant muscle and back strain.

One embodiment adds a stiffener to the hip strap directly over the lower back for extra support.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE INVENTION

Figure 1:
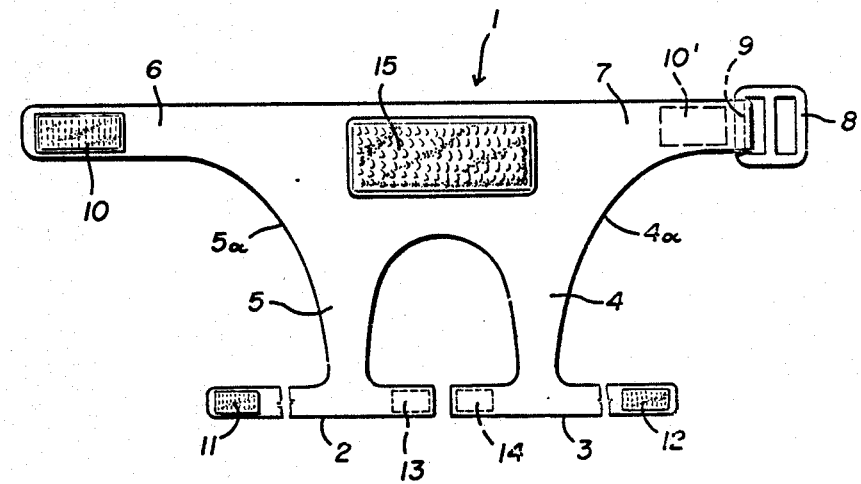
FIG. 1 is a front elevational view of the thigh mounted lower back support belt.
Figure 2:
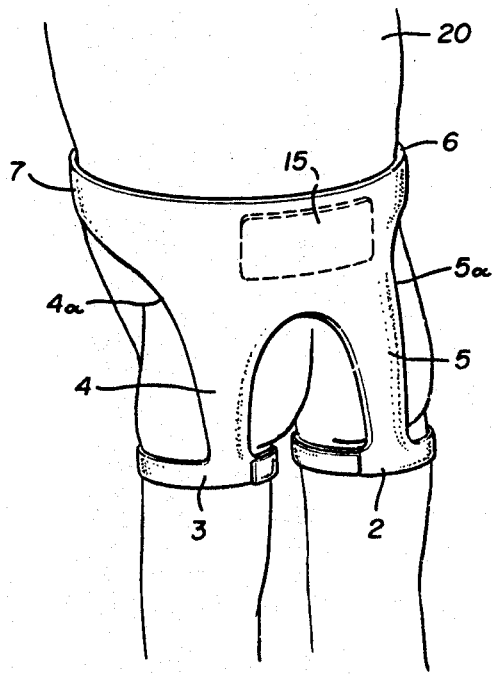
FIG. 2 is a top perspective view of the thigh mounted lower back support belt worn on the human being.
Figure 3:
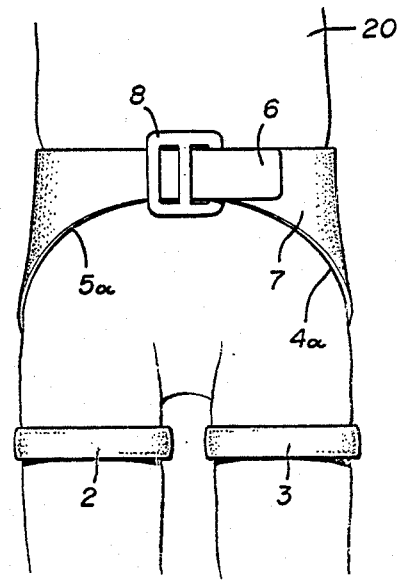
FIG. 3 is a front elevational view of the thigh mounted lower back support belt worn on the human being.

FIG. 1 shows the thigh mounted lower back support belt 1 in a fully opened position before mounting on the person. Thigh straps 2 and 3 wrap around the upper thighs and fasten by means of mat and loop fasteners 11, 13 and 12, 14 which could be Velcro ® or an equivalent. Traditional buckle means could also be used. Vertical buttocks straps 4 and 5 extend up individually from thigh straps 3 and 2, respectively, and attach to hip belt 6, 7 as shown here in a single piece of material. Hip belt 6, 7 fastens by means of mat and loop fasteners 10 and 10' working in cooperation with buckle 8. Buckle 8 in this embodment is sewn into belt 6, 7 by traditional stitches 9. The hip belt 6, 7 is, of course flexible and has a back segment joined to the upper ends of buttock straps 4 and 5 and extending across the person's lower back, as shown in FIG. 2, and left and right front segments which carry the fasteners 10 and 10'. As best seen in FIG. 1, the back segment of the hip belt has a substantially greater dimension vertically for most of its extent from left to right than the front segments. As shown in FIGS. 2 and 3, the hip belt 6, 7 is the top part of the present lower back support and is unattached except to the thigh straps 4 and 5. This lower back support has left and right outer edges 5a and 4a respectively extending up along the buttock straps 5 and 4 and diverging laterally outward from each other along the bottom of the back segment of hip belt 6, 7 and along the bottom of the front segments of the hip belt to pass over the top of a person's iliac crest, as shown in FIG. 3.

FIG. 1 shows an optional horizontally elongated stiffener 15 attached to the hip belt 6, 7 at the point over the lower back. This feature adds a direct contact support to the spine even while the person bends.

FIG. 2 shows human 20 wearing the thigh mounted lower back support belt. When the knees bend forward (not shown), vertical buttocks straps 4, 5 pull on hip belt 6, 7 and exert a force on the stomach (not shown) which in turn acts to straighten the pelvis and relieve the strain on the lower back.

FIG. 3 shows the front of human 20 wearing the thigh mounted lower back support belt. Hip belt 6, 7 is shown properly worn just above the top of the hips known as the iliac crest.

We claim:

1. A lower back support to be worn by a person to urge the spine straight while allowing natural movement of the upper torso, said support comprising:
    a pair of flexible left and right thigh straps constructed and arranged to be wrapped snugly around the person's corresponding thighs individually;
    a pair of flexible left and right buttock straps extending up individually from said left and right thigh straps, respectively;

and a flexible hip belt consisting essentially of a back segment joined to the upper ends of said buttock straps and dimensioned to extend across the person's lower back, left and right front segments joined to the opposite sides of said back segment and dimensioned to extend across the front of the person and overlap each other at the person's navel, and manually releasable fastener means on said front segments for holding them overlapped;

said back segment of the hip belt having a subtantially greater vertical dimension for most of its extent from left to right than said front segments;

said hip belt being the top part of said lower back support and being unattached except to said thigh straps;

said lower back support having left and right outer edges respectively extending up along said buttock straps and diverging laterally outward from each other and upward along the bottom of said back segment and along the bottom of said front segments to pass over the top of the person's iliac crest.

said thigh straps, when the person's knees are bent, moving forward and pulling on said buttock straps to pull down on said back segment of the hip belt and pull back on said overlapped front segments of the hip belt for restraining the forward curvature of the person's spine.

2. A back support according to claim 1 and further comprising a horizontally elongated stiffener on said back segment of the hip belt having its opposite side edges substantially aligned vertically with said left and right buttock straps, respectively.

* * * * *